United States Patent [19]

Baumann

[11] 4,368,535
[45] Jan. 11, 1983

[54] TOMOGRAPH FOR PRODUCING TRANSVERSE LAYER IMAGES

[75] Inventor: Heinz Baumann, Buckenhof, Fed. Rep. of Germany

[73] Assignee: Siemens Aktiengesellschaft, Berlin & Munich, Fed. Rep. of Germany

[21] Appl. No.: 329,656

[22] Filed: Dec. 11, 1981

Related U.S. Application Data

[63] Continuation of Ser. No. 233,385, Feb. 11, 1981, abandoned, which is a continuation of Ser. No. 948,426, Oct. 4, 1978, abandoned.

[30] Foreign Application Priority Data

Nov. 11, 1977 [DE] Fed. Rep. of Germany ....... 2750551

[51] Int. Cl.³ .............................................. H05G 1/10
[52] U.S. Cl. .................................................... 378/15
[58] Field of Search ................... 250/44 ST, 421, 422, 250/439 P; 378/15

[56] References Cited

U.S. PATENT DOCUMENTS

| | | | |
|---|---|---|---|
| 2,356,645 | 8/1944 | Atlee et al. ........................ | 250/421 |
| 2,925,499 | 2/1960 | Seidel ................................ | 250/421 |
| 3,970,853 | 7/1976 | Kuhl et al. ..................... | 250/445 T |
| 3,983,399 | 9/1976 | Cox et al. ..................... | 250/445 T |
| 3,999,073 | 12/1976 | Hounsfield et al. ........... | 250/445 T |
| 4,049,968 | 9/1977 | Distler et al. .................. | 250/445 T |
| 4,060,731 | 11/1977 | Rissi ................................. | 250/421 |
| 4,093,859 | 6/1978 | Davis et al. ..................... | 250/445 T |
| 4,192,997 | 3/1980 | Baumann ........................ | 250/445 T |

OTHER PUBLICATIONS

Coolidge, W. D., "Oil Immersed X-Ray Generating Outfits and Their Uses", General Electric Review, vol. 28, No. 3, p. 182, Mar., 1925.

Primary Examiner—Alfred E. Smith
Assistant Examiner—T. N. Grigsby
Attorney, Agent, or Firm—Hill, Van Santen, Steadman, Chiara & Simpson

[57] ABSTRACT

In the illustrative embodiment, an X-ray tube is attached to a rotary mounting, and the structural elements of the X-ray generator on the high voltage side are disposed on the rotary mounting in an oil-filled tank; for the transfer of energy, a rotating current coupling is provided between the rotary mounting and a stationary energy supply installation, e.g. a mains rectifier. The anode of the X-ray tube is connected to ground potential.

1 Claim, 6 Drawing Figures

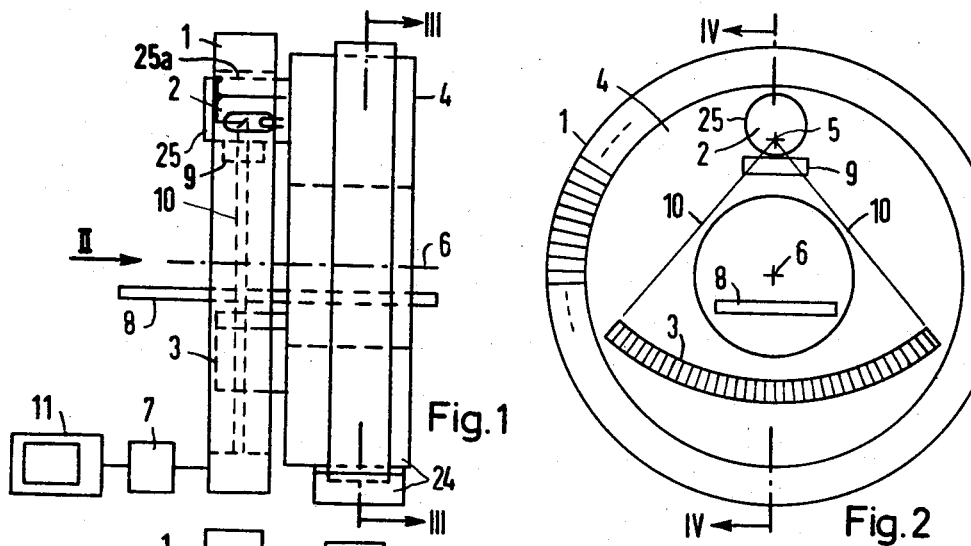
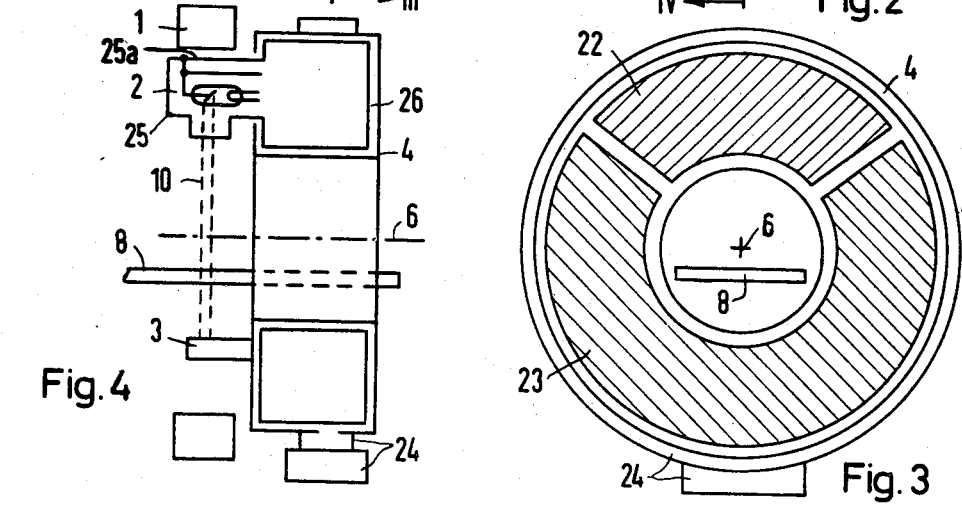
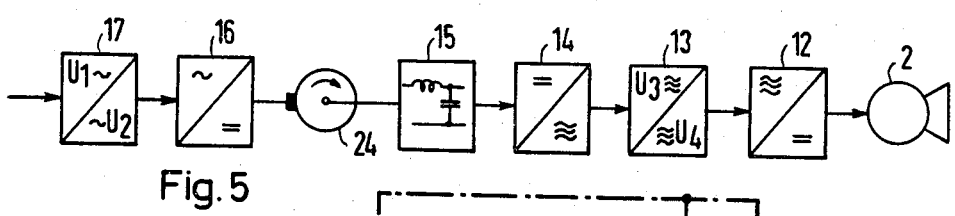
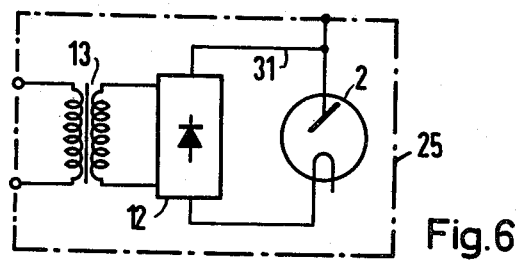

4,368,535

TOMOGRAPH FOR PRODUCING TRANSVERSE LAYER IMAGES

This is a continuation of application Ser. No. 233,385, filed Feb. 11, 1981, and now abandoned which is a continuation of Ser. No. 948,426, filed Oct. 4, 1978 now abandoned.

BACKGROUND OF THE INVENTION

The invention relates to tomographic apparatus for producing tranverse layer images of an exposure subject, with a radiation measuring arrangement with an X-ray source supplied by an X-ray generator which produces an X-ray beam penetrating the exposure subject, of which the cross-sectional extent perpendicular to the layer plane is the same as the layer thickness, with a radiation receiver which determines the radiation intensity behind the subject by scanning the projected X-ray beam, with a rotating frame for rotating the X-ray source in the layer plane to scan the exposure subject from different directions and with a measured value converter to transform the signals supplied by the radiation receiver into a layer image.

Efforts are being made to keep the image exposure time in a tomograph of this type as short as possible. The image exposure time is essentially determined by the duration of an exposure cycle; i.e., by the mechanical structure of the apparatus. A tomograph of the type specified at the outset is described, for instance, in German Auslegeschrift No. 24 37 710. In this known tomograph, the X-ray generator is disposed stationarily and is connected to the X-ray tube by high voltage cables. These cables must form a loop, so that the X-ray tube is mobile for scanning the exposure subject, and thus are detrimental to further reducing the exposure time.

SUMMARY OF THE INVENTION

The object underlying the invention is to develop a tomograph of the type specified at the outset with regard to its construction such as to render possible rapid movement of the X-ray source for scanning an exposure subject and thus render possible a short image build-up time.

According to the invention, this object is achieved by the fact that the structural elements of the X-ray generator on the high voltage side are disposed in an oil-filled tank mounted on the rotating frame, that for the transfer of energy a rotating current coupling is provided between the rotating frame and a stationary energy supply installation and that the anode of the X-ray tube is earthed (connected to ground). In the tomograph according to the invention, there is no need to run high voltage cables to the X-ray source. The coupling between the generator parts disposed on the rotary mounting and the energy supply installation may be made, by way of example, via a brush-slip ring arrangement. When the X-ray source is moved, therefore, there are no heavy cables to be moved with it, so that very short image build-up times are possible. Because the anode of the X-ray tube is earthed (grounded), the rays can issue near the end of the X-ray tube housing, in the case of an X-ray tube housing of small design, which means the tomograph of the type according to the invention has an advantageous mechanical construction.

The invention is explained in detail below with reference to an embodiment represented in the drawings; and other objects, features and advantages will be apparent from this detailed disclosure.

BRIEF DESCRIPTION OF THE DRAWINGS

FIG. 1 shows a lateral view of tomographic apparatus in accordance with the invention;
FIG. 2 shows a view of the tomograph in accordance with FIG. 1 taken in the direction of the arrow II;
FIG. 3 is a diagram based on the arrangement of parts in the plane III—III of FIG. 1;
FIG. 4 shows a section along line IV—IV in FIG. 2; and
FIGS. 5 and 6 show circuit diagrams to explain FIGS. 1 to 4.

DETAILED DESCRIPTION

The tomograph represented in FIGS. 1 to 4 has a circularly designed radiation receiver 1 consisting of a series of detector elements. It encloses an X-ray tube 2 and a collimator 3, these being attached to a rotating frame 4. With the X-ray tube 2 and the collimator 3 whose laminae are aligned with the focus 5 of the X-ray tube 2, the rotating frame 4 is rotatable about the axis 6 of the radiation receiver 1. The radiation receiver 1 is connected to a measured value converter 7 which from the output signals of the detector elements of the radiation receiver 1 produced while the X-ray tube 2 rotates through an angle of 360°, calculates the absorption values of predetermined points of a transverse layer of a patient lying on a couch 8. To form the X-ray beam penetrating the patient, a collimator 9 is attached to the X-ray tube 2 which collimates (diaphragms-in) a fan-shaped X-ray beam 10 whose spread is selected such that it penetrates the entire transverse layer to be examined of a patient lying on the couch 8 and that its dimension perpendicular to this layer is equal to the layer thickness. The absorption values calculated by the measured value converter 7 are reproduced on a video device 11 as a transverse layer image in the form of grey values. For the sake of simplicity, the measured value converter 7 and the video device 11 are only represented in FIG. 1.

From the circuit diagram according to FIG. 5, it is clear that the X-ray tube 2 is connected to a high voltage rectifier 12 whish is supplied by a high voltage transformer 13. The primary energy is supplied to the high voltage transformer 13 by an inverter 14 which is supplied via a direct voltage intermediate circuit 15, containing an LC filter, by a mains rectifier 16. Connected before the mains rectifier 16 is a further means adjusting member 17. The frequency of the inverter 14 is a medium frequency in the kHz range. The high voltage transformer 13 may therefore be made light-weight and small in construction.

The structural elements 2 and 12 to 15 are attached to the rotating frame 4, as will hereafter be explained in reference to FIG. 3. The high voltage transformer 13 with the high voltage rectifier 12 is here disposed in the space 22, FIG. 3, while the structural elements 14, 15 are located in the space 23. Energy is supplied to the direct voltage intermediate circuit 15 via a brush-slip ring arrangement 24, FIGS. 3 and 4. The structural elements 2, 12, 13, 14, 15 thus rotate at the same time as the rotating frame 4 rotates. There are no heavy cables at all to be moved during this rotation, so that the rotation can be effected very rapidly. The design of the X-ray generator according to FIG. 5 as a medium frequency generator produces a particularly light-weight and space-saving construction which renders a very short scanning time possible.

Disposing several X-ray tubes, instead of one single X-ray tube 2, on the rotating frame 4, angularly offset relative to one another, is conceivable within the scope of the invention. In this case, there is the further reduction of the scanning time as compared with the instance represented where a single X-ray tube is used, since the angle of rotation can be smaller than in the sample embodiment illustrated.

In FIG. 6 are shown by means of a circuit diagram, the X-ray tube 2, the high voltage rectifier 12 and the high voltage transformer 13. The anode of the X-ray tube 2 is connected to the housing 25, i.e. is earthed (connected to ground potential). The high voltage transformer 13 and rectifier 12 are contained in an oil-filled tank provided by housing 26, FIG. 4, and the connection lines between the X-ray tube 2 and the high voltage rectifier 12 are likewise located in oil in the housing 25.

Since the anode of the X-ray tube 2 is earthed, the X-ray tube 2 can be moved up with its end on the anode side very close to the walls at the end of the housing 25. It is also possible to provide the radiation exit opening of the housing 25 close to the end of the housing, which produces advantageous preconditions for the constructional design according to FIGS. 1 and 4. It is possible, in particular, to arrange the supply line 31, FIG. 6, on the anode side, of the X-ray tube 2 very close to the wall 25a of the housing 25 lying at the top in FIGS. 1 and 4, so that the distance between the X-ray tube 2 and the adjacent section of the radiation receiver 1 can be kept small. The distance between the supply line of the X-ray tube 2 on the cathode side and the wall of the housing 25 can be kept sufficiently great because of the arrangement of the X-ray tube 2.

Over and above the advantage of being able to design the tomograph structurally advantageously, the earthing (grounding) of the anode of the X-ray tube 2 also has the following advantages:

When an X-ray tube is used in a rotating anode design, the air gap between stator and rotor can, because of the earthed (grounded) anode, be kept very small. This is because there is virtually no potential difference arising between the earthed (grounded) stator and the rotor. The result of this is advantageous driving properties and a good heat discharge.

If an X-ray tube is used in a fixed gnode design, there is the possibility of providing an anode block through which water flows for the purpose of achieving good cooling properties. In this case, too, there is no potential difference arising between the water line and the anode.

It will be apparent that many modifications and variations may be effected without departing from the scope of the novel teachings and concepts of the present invention.

I claim as my invention:

1. In a tomographic apparatus for producing transverse layer images of an exposure subject having a stationary source of energy, an X-ray tube adapted to produce, when energized, an X-ray beam capable of penetrating the exposure subject, the cross-sectional extent of the X-ray beam perpendicular to the layer plane is the same as the layer thickness, a radiation receiver which senses the radiation intensity behind the subject by scanning the projected X-ray beam, a rotatable frame for rotating the X-ray tube in the layer plane to scan the exposure subject from different directions and a measured value converter to transform the signals delivered by the radiation receiver into a layer image, an improvement including an oil filled tank affixed to the rotatable frame, said oil filled tank includes means for generating high voltage, said means for generating includes a low voltage input and a high voltage output, said high voltage output is connected to a cathode of the X-ray tube and an anode of the X-ray tube is connected to ground potential, rotating current coupling means adapted to continuously, electrically, connect said low voltage input of said means for generating high voltage to the stationary source of energy as the rotatable frame is being rapidly rotated about the exposure subject thereby continuously providing energy to said means for generating such that the X-ray tube may be energized while the frame is being rotated through an angle of 360° in order to minimize exposure time, wherein the radiation receiver has a toroidal shape with an interior cylindrical surface and the axis of rotation of the rotatable frame corresponds to an axis of symmetry of the radiation receiver, said improvement comprising further, a housing for the X-ray tube, said housing is affixed to the frame and is adapted to support the X-ray tube with an anode side of the X-ray tube located adjacent an end of said housing and with a side wall of said housing positioned adjacent to and radially inwardly from the interior cylindrical surface of the radiation receiver, a grounded wire connected to said anode is positioned along an interior surface of said side wall such that said X-ray tube can be located relatively close to an adjacent region of the interior cylindrical surface of the radiation receiver.

* * * * *